(12) United States Patent
Pemper et al.

(10) Patent No.: US 7,402,797 B2
(45) Date of Patent: Jul. 22, 2008

(54) METHOD AND APPARATUS FOR DETERMINING ALUMINUM CONCENTRATION IN EARTH FORMATIONS

(75) Inventors: Richard R. Pemper, Sugar Land, TX (US); Pingjun Guo, Pearland, TX (US)

(73) Assignee: Baker Hughes Incorporated, Houston, TX (US)

( * ) Notice: Subject to any disclaimer, the term of this patent is extended or adjusted under 35 U.S.C. 154(b) by 349 days.

(21) Appl. No.: 11/223,352

(22) Filed: Sep. 9, 2005

(65) Prior Publication Data

US 2006/0033023 A1    Feb. 16, 2006

Related U.S. Application Data

(63) Continuation-in-part of application No. 10/916,921, filed on Aug. 12, 2004, now Pat. No. 7,205,535.

(51) Int. Cl.
*G01V 5/10*    (2006.01)
(52) U.S. Cl. .................................................. 250/269.6
(58) Field of Classification Search ............. 250/269.6, 250/269.8
See application file for complete search history.

(56) References Cited

U.S. PATENT DOCUMENTS

| | | | | |
|---|---|---|---|---|
| 3,781,545 A | * | 12/1973 | Paap et al. | 376/163 |
| 4,390,783 A | | 6/1983 | Grau | 250/270 |
| 4,394,574 A | | 7/1983 | Grau et al. | 250/262 |
| 4,712,424 A | | 12/1987 | Herron | 73/152 |
| 4,773,264 A | * | 9/1988 | Herron | 73/152.05 |
| 4,810,876 A | * | 3/1989 | Wraight et al. | 250/256 |
| 4,916,616 A | * | 4/1990 | Freedman et al. | 702/13 |
| 5,471,057 A | | 11/1995 | Herron | 250/269.6 |

OTHER PUBLICATIONS

Pemper et al.; *Hydraulic fracture evaluation with multiple radioactive tracers*, Geophysics, vol. 53, No. 10 (Oct,. 1988), pp. 1323-1333, 12 Figs., 3 Tables.
Pemper et al.; *A New Generation Natural Gamma Ray Spectroscopy Logging System*, E027, 17th European Formation Evaluation Symposium (SPWLA), Amsterdam, The Netherlands, Jun. 3-7, 1996, 1 Fig.
Culver et al.; *Carbon/Oxygen (C/O) Logging Instrumentation*, SPE 4640, Society of Petroleum Engineers Journal, Oct. 1974, pp. 463-470.

(Continued)

*Primary Examiner*—Constantine Hannaher
(74) *Attorney, Agent, or Firm*—Madan, Mossman & Sriram, P.C.

(57) ABSTRACT

Elemental analysis of an earth formation (including Aluminum) is obtained using measurements from a gamma ray logging tool. The inelastic spectrum of Aluminum is determined from measurements made in a water tank. From the elemental analysis, an estimate of the mineralogy of the formation is made treating the problem as one of Linear Programming (maximizing an objective function subject to equality and/or inequality constraints.

22 Claims, 8 Drawing Sheets

OTHER PUBLICATIONS

Westaway et al.; *The Gamma Spectrometer Tool Inelastic and Capture Gamma-Ray Spectroscopy for Reservoir Analysis*, SPE 9461, 55th Annual Fall Technical Conference and Exhibition of the Society of Petroleum Engineers of AIME, Dallas, Texas, Sep. 21-24, 1980.

R. C. Hertzog; *Laboratory and Field Evaluation of an Inelastic-Netron-Scattering and Capture Gamma Ray Spectroscopy Tool*, SPE 7430, 53rd Annual Fall Technical Conference and Exhibition of the Society of Petroleum Engineers of AIME, Houston, Texas, Oct. 1-3, 1978.

B. A. Roscoe et al.; *Statistical Precision of Neutron-Induced Gamma Ray Spectroscopy Measurements*, The Log Analyst, Nov.-Dec. 1984; pp. 538-545, 10 Figs.

J. A Grau et al.; *Prompt γ-Ray Spectral Analysts of Well Data Obtained with NaI (TI) and 14 MeV Netrons*, Nucl. Geophys. vol. 1, No. 2, 19879, pp. 157-165, 9 Figs. 3 Tables.

R. Hertzog; *Geochemical Logging With Spectrometry Tools.*, SPE Formation Evaluation, Jun. 1989, pp. 153-162, 6 Figs.

\* cited by examiner

METHOD AND APPARATUS FOR DETERMINING ALUMINUM CONCENTRATION IN EARTH FORMATIONS

CROSS-REFERENCES TO RELATED APPLICATIONS

This application is a continuation-in-part of U.S. patent application Ser. No. 10/916,921 filed on Aug. 12, 2004 now U.S. Pat. No. 7,205,535.

BACKGROUND OF THE INVENTION

1. Field of the Invention

The present invention is in the field of gamma ray testing of geological formations. In particular, the invention determines the elemental composition and mineralogy of a formation from recorded spectra.

2. Description of the Related Art

Well logging systems have been utilized in hydrocarbon exploration for many years. Such systems provide data for use by geologists and petroleum engineers in making many determinations pertinent to hydrocarbon exploration. In particular, these systems provide data for subsurface structural mapping, defining the lithology of subsurface formations, identifying hydrocarbon-productive zones, and interpreting reservoir characteristics and contents. Many types of well logging systems exist which measure different formation parameters such as conductivity, travel time of acoustic waves within the formation and the like.

One class of systems seeks to measure incidence of nuclear particles on the well logging tool from the formation for purposes well known in the art. These systems take various forms, including those measuring natural gamma rays from the formation. Still other systems measure gamma rays in the formation caused by bursts of neutrons into the formation by a neutron source carried by the tool and pulsed at a preselected time interval.

In these nuclear well logging systems, reliance is made upon the physical phenomenon that the energies of gamma rays given off by nuclei resulting from natural radioactive decay or induced nuclear radiation are indicative of the presence of certain elements within the formation. In other words, formation elements will react in predictable ways, for example, when high-energy neutrons on the order of 14.2 MeV collide with the nuclei of the formation elements. Different elements in the formation may thus be identified from characteristic gamma ray energy levels released as a result of this neutron bombardment. Thus, the number of gamma rays at each energy level will be functionally related to the quantity of each element present in the formation, such as the element carbon, which is present in hydrocarbons. The presence of gamma rays at about 2.2 MeV energy level in the capture spectrum may for example, indicate the presence of hydrogen, whereas a predominance of gamma rays having energy levels of about 1.779 and 2.212 MeV in the inelastic spectrum, for example, may indicate the presence of silicon and aluminum respectively.

The measurement of neutron population decay rate is made cyclically. The neutron source is pulsed for 20-50 microseconds to create a neutron population. Neutrons leaving the pulsed source interact with the surrounding environment and are slowed down. In a well logging environment, collisions between the neutrons and nuclei of atoms in the surrounding fluid and formation act to slow these neutrons. Such collisions may impart sufficient energy to these atoms to leave them in an excited state, from which after a very short time gamma rays are emitted as the atom returns to a stable state. Such emitted gamma rays are labeled "inelastic gamma rays." As the neutrons are slowed to the thermal state (less than 0.1 eV), they may be captured by atoms in the surrounding matter. Atoms capturing such neutrons are also caused to be in an excited state, and after a short time gamma rays are emitted as the atom returns to a stable state. Gamma rays emitted due to this neutron capture reaction are labeled capture gamma rays. In wireline well logging operations, as the neutron source is pulsed and the measurements made, the subsurface well logging instrument is continuously pulled up through the borehole. This makes it possible to evaluate formation characteristics over a range of depths.

Depending on the material composition of the earth formations proximal to the instrument, the thermal neutrons can be absorbed, or "captured", at various rates by certain types of atomic nuclei in the earth formations. When one of these atomic nuclei captures a thermal neutron, it emits a gamma ray, which is referred to as a "capture gamma ray".

Prior art methods exist for determining attributes of a formation from logging results. Reference is made to U.S. Pat. No. 4,712,424, to Herron, U.S. Pat. No. 4,394,574, to Grau et al., U.S. Pat. No. 4,390,783, to Grau for methods for analysis of nuclear data. Methods of decomposing obtained spectra into constituent spectra have been discussed, for instance, in SPE 7430 by Hertzog, Grau and Schweitzer(1987). The methods discussed in these papers correct an obtained inelastic spectrum by subtracting a background spectrum. Statistical analysis of obtained spectra is discussed by Roscoe et al., November-December, 1987, The Log Analyst. Reference is also made to paper E027 of the SPWLA by Pemper et al., SPE paper 4640 of Culver et al., and to "Hydraulic fracture evaluation with multiple radioactive tracers" by Pemper et al., (Geophysics, 1988).

Aluminum is one of the most important elements in lithology and mineral analysis. Many of the minerals encountered in petroleum exploration are associated with aluminum. Accurate determination of aluminum content can greatly improve formation mineral characterization process. Listed below are examples of aluminum rich minerals.

Feldspars: $NaAlSI_3O_8$ (albite),
$CaAl_2Si_2O_8$ (anorthite),
$KAlSi_3O_8$ (orthoclase, microcline)

Clays: $Al_2Si_2O_5(OH)_4$ (Kaolinite),
$(Na,Ca)(Al,Mg)_6(Si_4O_{10})_3(OH)_6$—$nH_2O$ (montmorillonite)
$(Fe,Mg,Al)_6(Si,Al)_4O_{10}(OH)_8$(chlorite)
$(K,H_3O)(Al,Mg,Fe)_2(Si,Al)_4O_{10}[(OH)_2,(H_2O)]$ (illite)

Micas $KAl_2(AlSi_3O_{10})(F,OH)_2$ (muscovite)
$K(Fe,Mg)_3AlSi_3O_{10}(F,OH)_2$ (biotite)
$(K,Na)(Fe,Al,Mg)_2(Si,Al)_4O_{10}(OH)_2$ (glauconite)

As noted in the *Encyclopedia Britannica*, identifying the various minerals, particularly those containing Aluminum, provides valuable information about mechanisms by which minerals of different sizes are transported and deposited, and also about the chemical conditions that permit precipitation of various authigenic minerals. As temperature and pressure increase with the progression of diagenesis, clay minerals in sediments under these circumstances change to those stable under given conditions. Therefore, certain sensitive clay minerals may serve as indicators for various stages of diagenesis. Typical examples are the crystallinity of illite, the polytypes of illite and chlorite, and the conversion of smectite to illite. Data indicate that smectite was transformed into illite through interstratified illite-smectite mineral phases as diagenetic processes advanced. Much detailed work has been devoted to the study of the conversion of smectite to illite in lower Cenozoic-Mesozoic sediments because such conversion appears to be closely related to oil-producing processes.

One prior art method for identification of aluminum (Al) uses activation analysis. Al activation requires an additional activation source and gamma ray detectors and is discussed, for example, in SPE 16792 of Hertzog et al. The natural Al isotope, $Al^{27}$, absorbs thermal neutrons and produces $Al^{28}$ in an excited state.

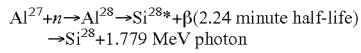
$Al^{27}+n \rightarrow Al^{28} \rightarrow Si^{28*}+\beta$(2.24 minute half-life)
$\rightarrow Si^{28}+1.779$ MeV photon Disadvantages of activation measurement are instrument complexity, low logging speed, and interference from activation of other elements in the formation such as manganese.

U.S. Pat. No. 5,471,057 to Herron describes a method for indirectly determining Al yield by modifying the iron gamma ray yield in thermal neutron capture measurement. This method is not accurate and suffers from low measurement sensitivity as aluminum has low thermal neutron absorption cross section of 0.23 barns. Although the Al capture spectrum resembles some of the iron spectrum features, the assumption that a constant correlation exists between aluminum and iron contents is often not true.

There is a need for a more complete analysis of the obtained gamma ray spectra. A separation of inelastic and capture gamma ray spectra yields a more complete understanding of the elemental composition of a geological structure. Consequently, an advantage can be obtained through a combined analysis of both inelastic and capture spectra in terms of their formation constituents. Such a method should give physically realistic analyses. The present invention fulfills this need.

SUMMARY OF THE INVENTION

One embodiment of the invention is a method of analyzing an earth formation. The method includes conveying a tool into a borehole in the earth formation and pulsing the formation with radiation from the tool. Gamma rays resulting from interaction of the pulsed radiation with nuclei of more than one element (including Aluminum) in the formation are detected. From a determined spectrum of the gamma rays, en elemental concentration of Aluminum and at least one additional element in the formation is determined. The radiation may include neutrons. The detected gamma rays may include inelastic gamma rays and/or capture gamma rays. The determined spectrum may include an inelastic spectrum. The estimation of the elemental concentration may include using an inelastic spectrum for Aluminum. The inelastic spectrum of Aluminum may be estimated using measurements made in a water tank. The method may further involve defining a set of mineral constituents of the earth formation and solving a constrained optimization problem to determine a relative fraction of each of the possible mineral constituents. The constrained optimization problem may be a Linear Programming problem. The set of mineral constituents may include albite, anorthite, orthoclase, microcline, kaolinite, montmorillonite, chlorite, ilite, muscovite, biotite, and/or glauconite. From the determined mineral constituents, an indication of diagenesis and/or source rock maturation can be obtained.

Another embodiment of the invention is an apparatus for evaluating an earth formation. The apparatus includes a tool conveyed in a borehole in the earth formation. The tool includes a radiation source which pulses the earth formation with radiation and at least one detector which detects gamma rays resulting from interaction of the radiation with nuclei of Aluminum and at least one other element in the formation. A processor determines a spectrum of the detected gamma rays and estimates from the determined spectrum an elemental concentration of Aluminum and at least one additional element. The radiation source may be a neutron source. The detected gamma rays may include inelastic gamma rays and/or capture gamma rays. The determined spectrum may include an inelastic spectrum. The processor may estimate the elemental concentration by using an inelastic spectrum for Aluminum. The apparatus may further include a device which is used for measuring the inelastic spectrum for Aluminum. The processor may further define a set of possible mineral constituents for the earth formation and solve a constrained optimization problem to determine a relative fraction of each of the possible mineral constituents. The set of mineral constituents may include albite, anorthite, orthoclase, microcline, kaolinite, montmorillonite, chlorite, ilite, muscovite, biotite, and/or glauconite. From the determined mineral constituents, the processor may obtain an indication of diagenesis and/or source rock maturation. The tool may be conveyed into the borehole using a wireline, drilling tubular or a slickline. The borehole may be an open-hole.

Another embodiment of the invention is a computer readable medium for use with an apparatus for evaluating an earth formation. The apparatus includes a tool conveyed in a borehole in the earth formation. The tool includes a radiation source which pulses the earth formation with radiation and at least one detector which detects gamma rays resulting from interaction of the radiation with nuclei of Aluminum and at least one additional element. The medium includes instructions which enable a processor to determine a spectrum of the detected gamma rays and to estimate from the determined spectrum an elemental concentration of Aluminum and at least one additional element from the plurality of elements.

BRIEF DESCRIPTION OF THE DRAWINGS

The present invention is best understood with reference to the accompanying figures in which like numerals refer to like elements and in which.

DETAILED DESCRIPTION OF THE INVENTION

Figure 1:
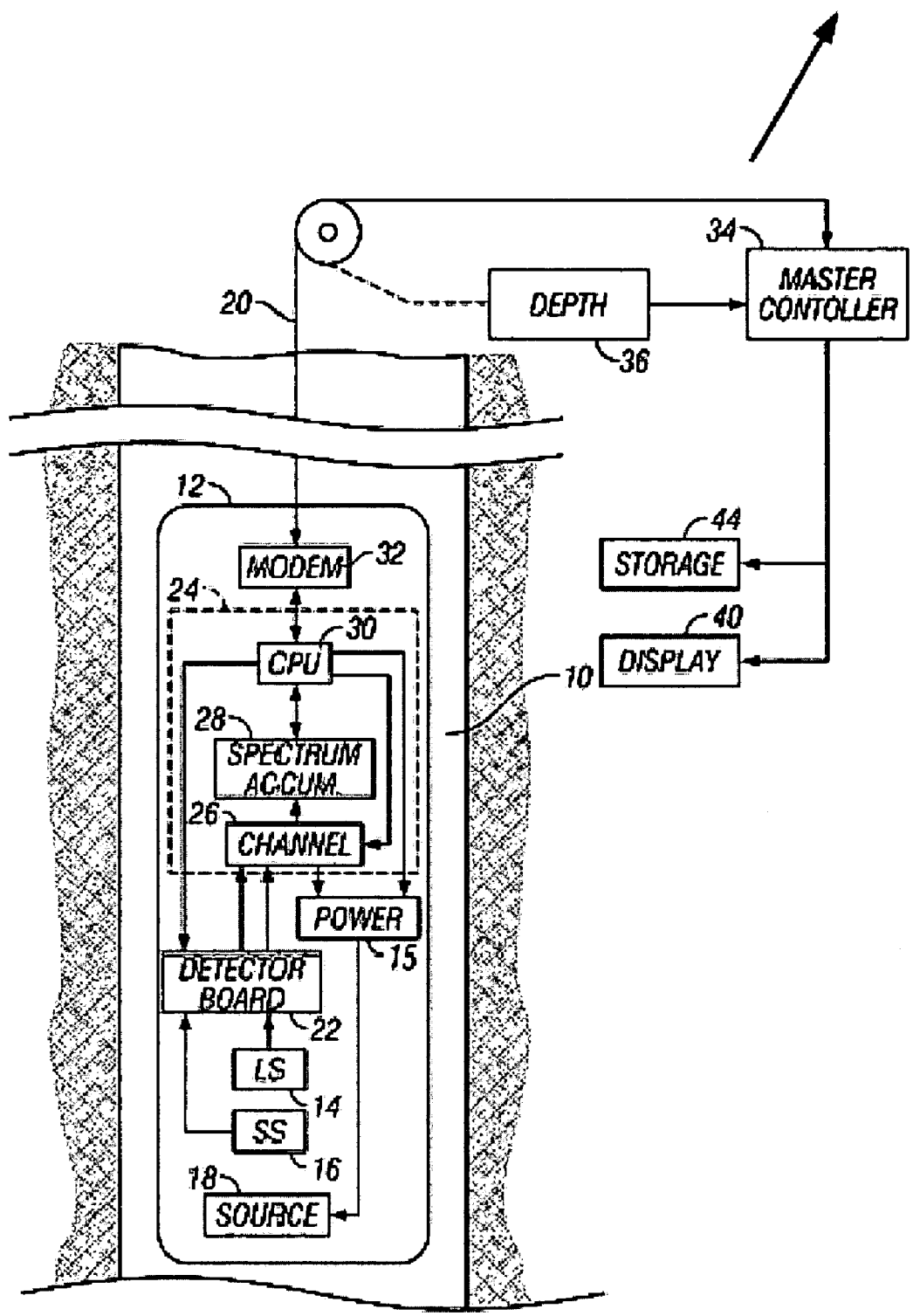
FIG. 1 illustrates a nuclear well logging configuration in accordance with the present invention.

Referring now to the drawings in more detail, and particularly to FIG. 1, there is illustrated a nuclear well logging configuration in accordance with the present invention. Well 10 penetrates the earth's surface and may or may not be cased depending upon the particular well being investigated. Disposed within well 10 is subsurface well logging instrument 12. The system diagramed in FIG. 1 is a microprocessor-based nuclear well logging system using multi-channel scale analysis for determining the timing distributions of the detected gamma rays. Well logging instrument 12 includes at least one detector and may include a long-spaced (LS) detector 14, short-spaced (SS) detector 16 and pulsed neutron source 18. In an exemplary embodiment, LS and SS detectors 14 and 16 are comprised of bismuth-germanate (BGO) crystals coupled to photomultiplier tubes. To protect the detector systems from the high temperatures encountered in boreholes, the detector system may be mounted in a Dewar-type flask. Also, in an exemplary embodiment, source 18 comprises a pulsed neutron source using a D-T reaction wherein deuterium ions are accelerated into a tritium target, thereby generating neutrons having an energy of approximately 14 MeV. The filament current and accelerator voltage are supplied to source 18 through power supply 15. Cable 20 suspends instrument 12 in well 10 and contains the required conductors for electrically connecting instrument 12 with the surface apparatus.

The outputs from LS and SS detectors 14 and 16 are coupled to detector board 22, which amplifies these outputs and compares them to an adjustable discriminator level for passage to channel generator 26. Channel generator 26 converts the output pulse heights to digital values, which are accumulated into pulse height spectra, in which the pulses are sorted according to their amplitudes into a discrete array of bins. The bins uniformly divide the entire amplitude range. These pulse height spectra are accumulated in registers in the spectrum accumulator 28, the spectra being sorted according to their type: total, capture, or background. The inelastic spectrum is derived from them. After a pulse height spectrum has been accumulated, CPU 30 controls the transfer of the accumulated data to the modem 32, which is coupled to cable 20 for transmission of the data over a communication link to the surface apparatus. To be explained later are further functions of CPU 30 in communicating control commands which define certain operational parameters of instrument 12 including the discriminator levels of detector board 22, and the filament current and accelerator voltage supplied to source 18 by power supply 15.

The surface apparatus includes master controller 34 coupled to cable 20 for recovery of data from instrument 12 and for transmitting command signals to instrument 12. There is also associated with the surface apparatus depth controller 36 which provides signals to master controller 34 indicating the movement of instrument 12 within well 10. An input terminal may be coupled to master controller or processor 34 to allow the system operator to provide selected input into master controller 34 for the logging operation to be performed by the system. Display unit 40, and storage unit 44 coupled to the master controller 34 may be provided. The data may also be sent by a link to a remote location. Processing may be done either by the surface processor, at the remote site, or by a downhole processor.

In a well logging operation such as is illustrated by FIG. 1, master controller 34 initially transmits system operation programs and command signals to be implemented by CPU 30, such programs and signals being related to the particular well logging operation. Instrument 12 is then caused to traverse well 10 in a conventional manner, with source 18 being pulsed in response to synchronization signals from channel generator 26. Typically, source 18 is pulsed at a rate of 10,000 bursts/second (10 kHz). This, in turn, causes a burst of high-energy neutrons on the order of 14 MeV to be introduced into the surrounding formation to be investigated. In a manner previously described, this population of high energy neutrons introduced into the formation will cause the generation of gamma rays within the formation which at various times will impinge on LS and SS detectors 14 and 16. As each gamma ray thus impinges upon the crystal-photomultiplier tube arrangement of the detectors, a voltage pulse having an amplitude functionally related to the energy of the particular gamma ray is delivered to detector board 22. It will be recalled that detector board 22 amplifies each pulse and compares them to an adjustable discriminator level, typically set at a value corresponding to approximately 100 keV. If such pulse has an amplitude corresponding to an energy of at least approximately 100 keV, the voltage pulse is transformed into a digital signal and passed to channel generator 26.

Figure 2:
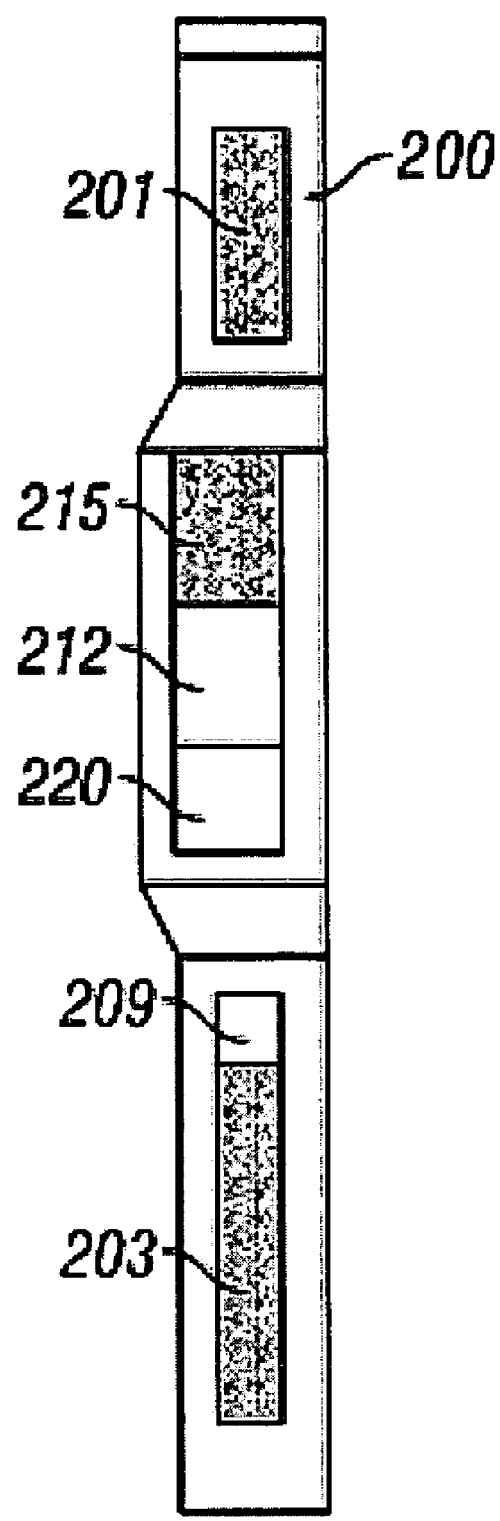
FIG. 2 shows an instrument suitable for use with the present invention.

FIG. 2 illustrates a schematic diagram of an instrument suitable for use with the present invention. The Formation Lithology Spectrometer (FLS™) is a wireline instrument designed to provide formation mineralogical information, shale identification, and clay typing. The enhanced mineralogical data obtained from the FLS also enables enhanced porosity measurements. The present invention is usable in open-hole wireline logging systems. In a typical embodiment, the present invention uses the ECLIPS™ acquisition system of Baker Hughes Incorporated. Alternatively, the present invention can be used, for example, with the FOCUS system of Baker Hughes, Incorporated. Also, under most conditions, the FLS is run in combination with Gamma Ray/ Spectralog, Neutron, and Density nuclear tools in addition to tools such as resistivity, acoustics, NMR and others. The FLS utilizes an axial pulsed neutron generator of the same type as that used in the reservoir performance monitor instruments. Thus, there are no special storage or transportation requirements except those of a regulatory nature associated with pulsed neutron generators. The logging speed is dependent upon the environment. A typical logging speed is in the range of 15-30 ft/min.

The FLS measurement device of FIG. 2 employs the principle of neutron-induced gamma ray spectroscopy. FLS component parts are encapsulated within wireline device casing 200. The neutron source of the present invention is typically a pulsed neutron source. The use of a pulsed neutron source is advantageous over the use of a chemical neutron source due to its ability to generate inelastic gamma rays over a wider range of energies. It also allows a spectrum of capture gamma rays to be generated which is free from inelastic gamma ray contamination, which can also be corrected for background activation gamma rays. Neutron source 209 discharges high-energy bursts of neutrons into the surrounding formation. The electronic pulsed neutron generator is typically operated at a rate of approximately 10,000 Hz, so that each burst takes place within a 100 microsecond window. Gamma rays produced via interaction of the discharged neutrons and the formation are detected at the scintillation detector 212 attached to acquisition and telemetry electronics 215. Power supply 201 enables the FLS device. Electronics 203 enables the neutron source. A shield 220 attenuates the neutron flux propagating directly from the source to the detector as well as attenuating gamma rays generated within the shield.

Figure 3:
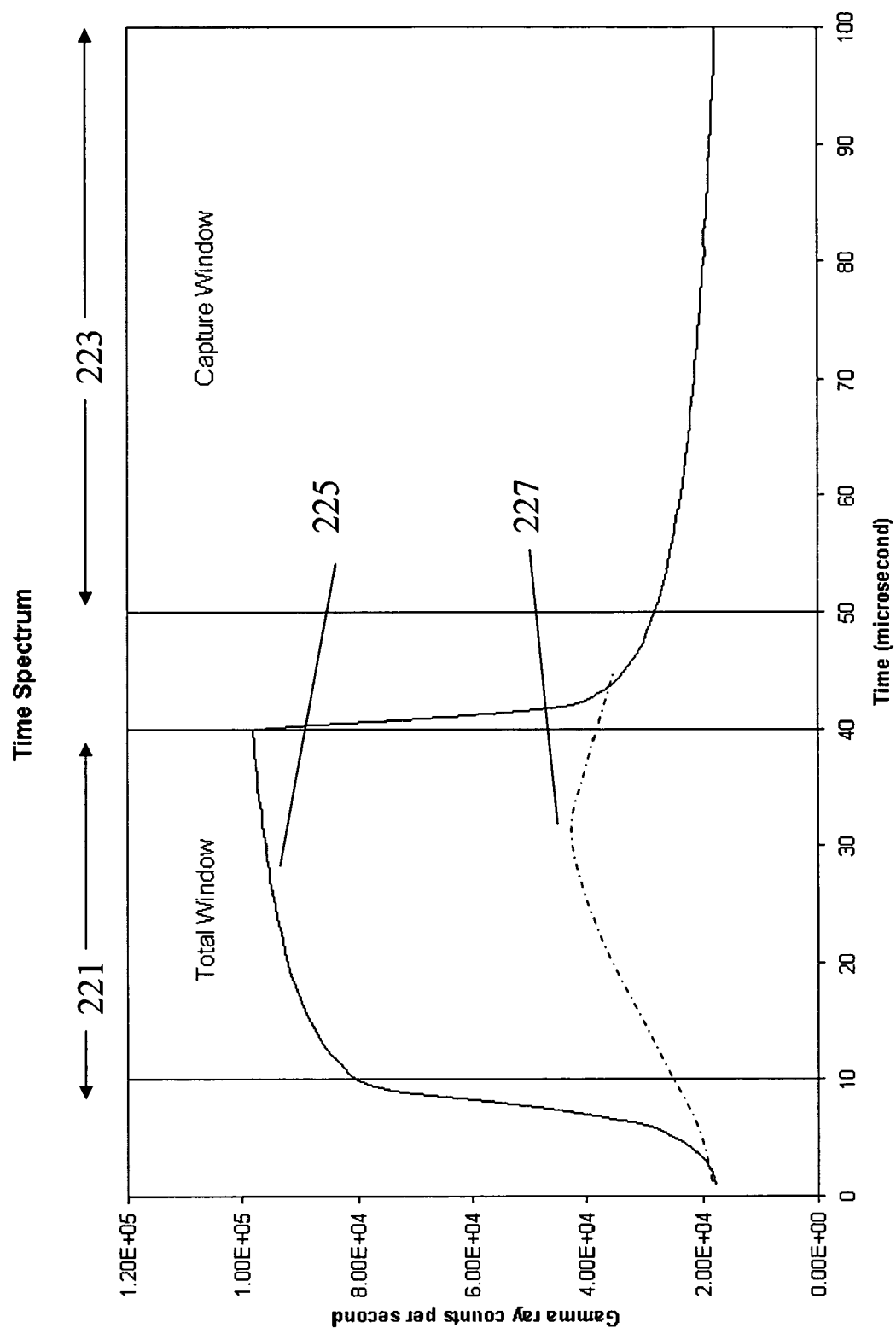
FIG. 3 shows the basic timing of the pulsed neutron source and the produced gamma rays.

FIG. 3 illustrates the basic timing of the pulsed neutron source and the produced gamma rays. Time is displayed along the x-axis in microseconds. The gamma ray counts per second (cps) is displayed along the y-axis. The neutron burst is over a time interval 221 and defines a first-detector-gate interval, referred to as the "burst gate" or inelastic gate. A total spectrum 225 of gamma rays resulting from both inelastic neutron scattering and capture gamma ray scattering is produced during the active duration of the neutron source, and the timing of the inelastic gate enables obtaining the total spectrum. In the example of FIG. 3, the number of counts rises significantly (typically to $10^5$) during the inelastic gate, which extends approximately from 10 μs to 40 μs. The deactivation of the neutron source causes the inelastic gamma rays to disappear from the count almost immediately. A "dead-zone" is shown at a point substantially coincident with deactivation of the neutron source. This dead-zone extends approximately from 40 μs to 50 μs. The counts obtained during this interval are not recorded. The dead-zone is followed by a "capture gate" 223. The capture gate contains gamma rays substantially due to captured neutrons from the surrounding formation.

In an exemplary embodiment of the present invention, energized neutrons are injected from a pulsed neutron source 209 into a surrounding formation. The scintillation detector records the spectrum over a predetermined time interval. During the inelastic gate, a total spectrum 225 of gamma rays is obtained from the formation layer. A portion of the total spectrum 227 is attributable to capture gamma rays. During a capture gate, a capture spectrum of gamma rays is obtained from the formation layer. A determinable factor of the capture spectrum is subtracted from the obtained total spectrum to derive a spectrum substantially representative of an inelastic spectrum only. The elemental contribution to the inelastic spectrum and the capture spectrum can then be obtained by determining a set of constituent spectra from the inelastic spectrum and a set of constituent spectra from the capture spectrum. These constituent spectra are characteristic of individual elements and are referred to as "elemental standards." An operator versed in the arts can then use the determined elemental contributions to determine a parameter of the surrounding formation.

Figure 4:
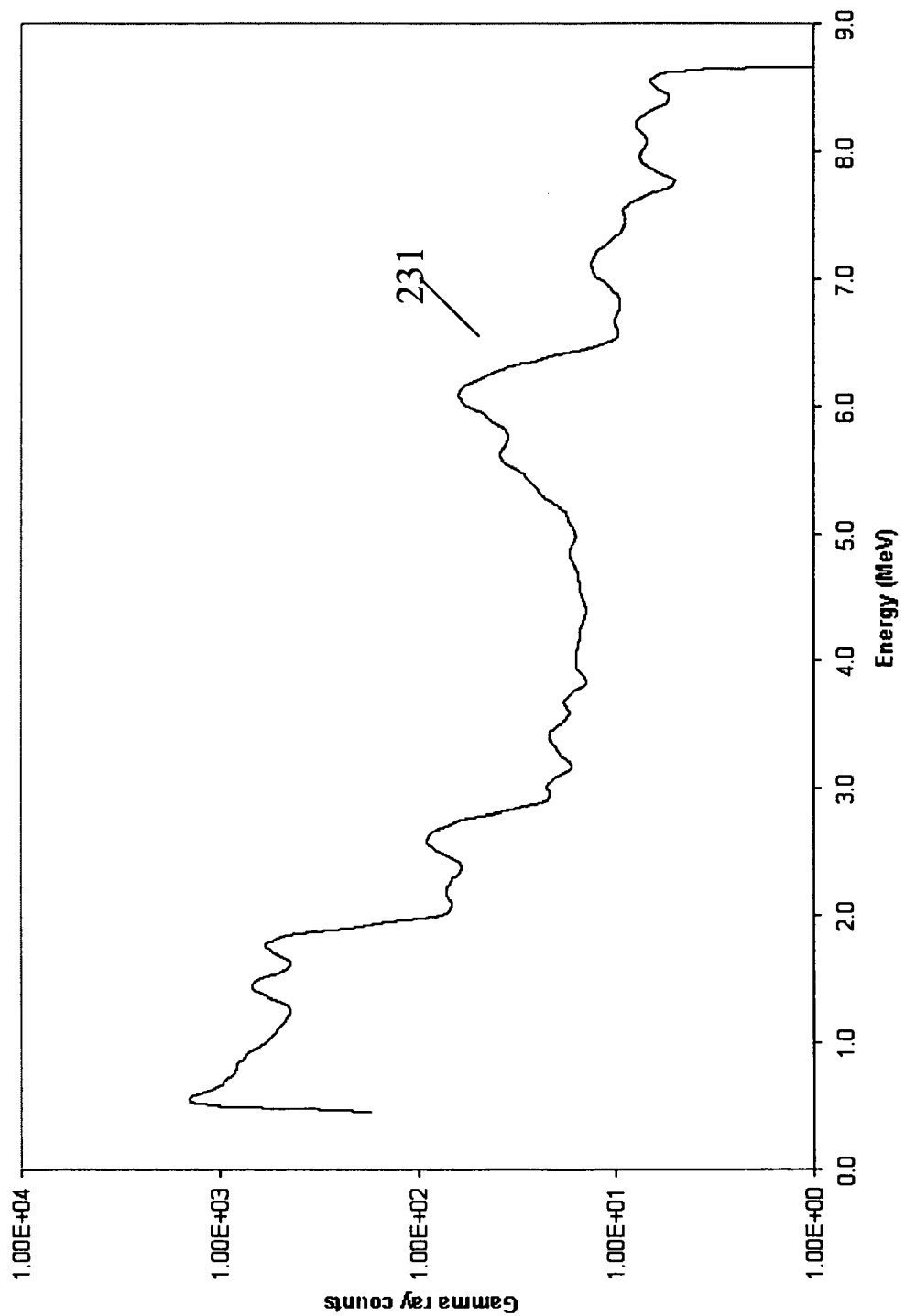
FIG. 4 background spectra measured by a logging tool in an intermediate igneous block.

FIG. 4 shows the background spectrum with the logging tool in a 6" (15.24 cm) borehole in the intermediate igneous block. The spectrum was measured over a entire time interval of 3000 μs. Note that the abscissa of FIG. 4 is the energy of the gamma rays while the ordinate is the number of gamma ray counts.

Figure 5:
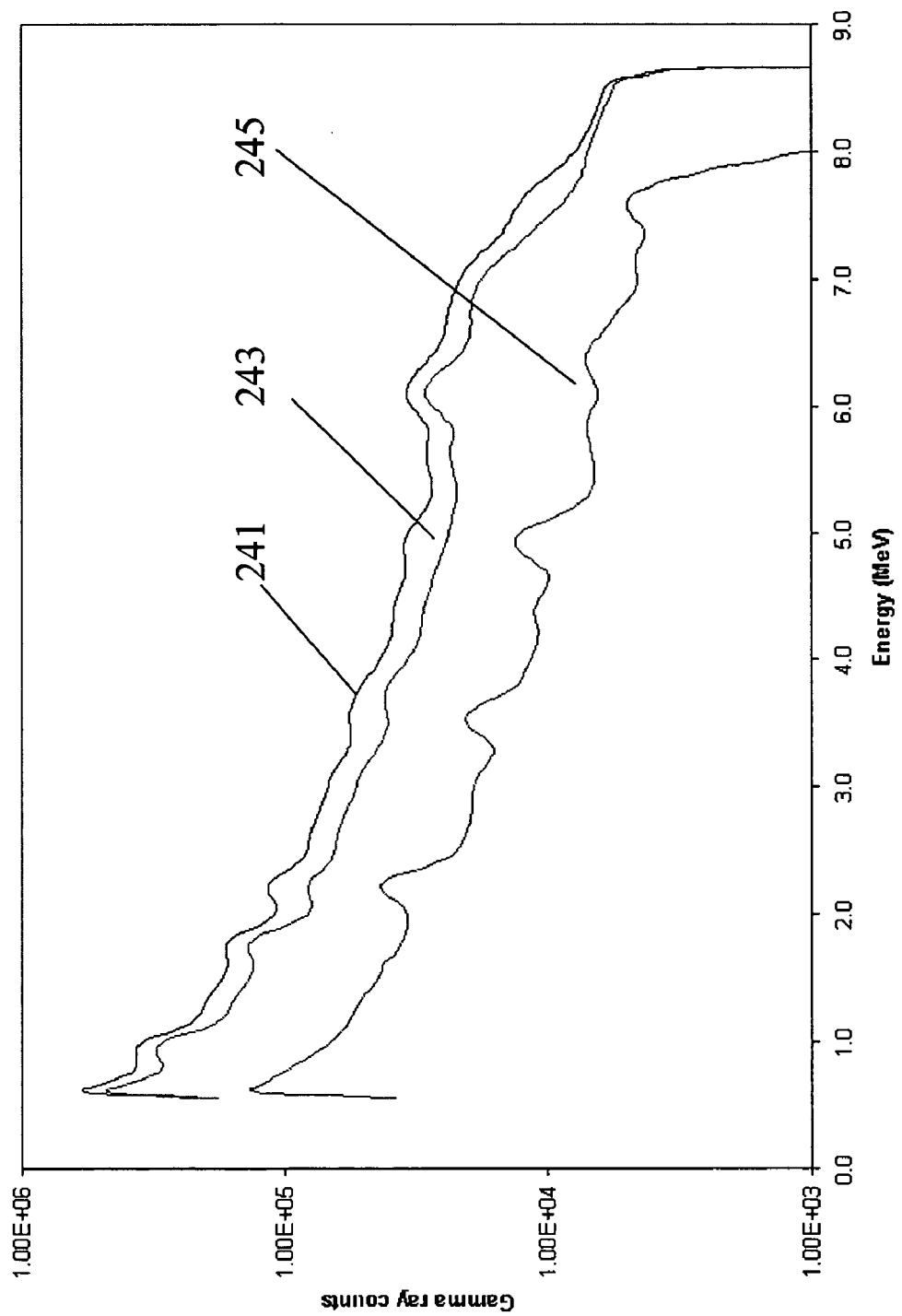
FIG. 5 shows the total spectrum, the inelastic spectrum and the capture spectrum measured in an intermediate igneous block.

FIG. 5 shows the total spectrum 241 measured with the tool placed in the borehole of the intermediate igneous block, 245 is the capture spectrum in the intermediate igneous block and 243 is the inelastic spectrum in the intermediate igneous block determined as the difference between the total spectrum and a fraction of the capture spectrum. In the present invention, the capture spectrum is multiplied by a scale factor (in the range of 0.8-1.2 or so) before subtraction from the total spectrum.

Figure 6:
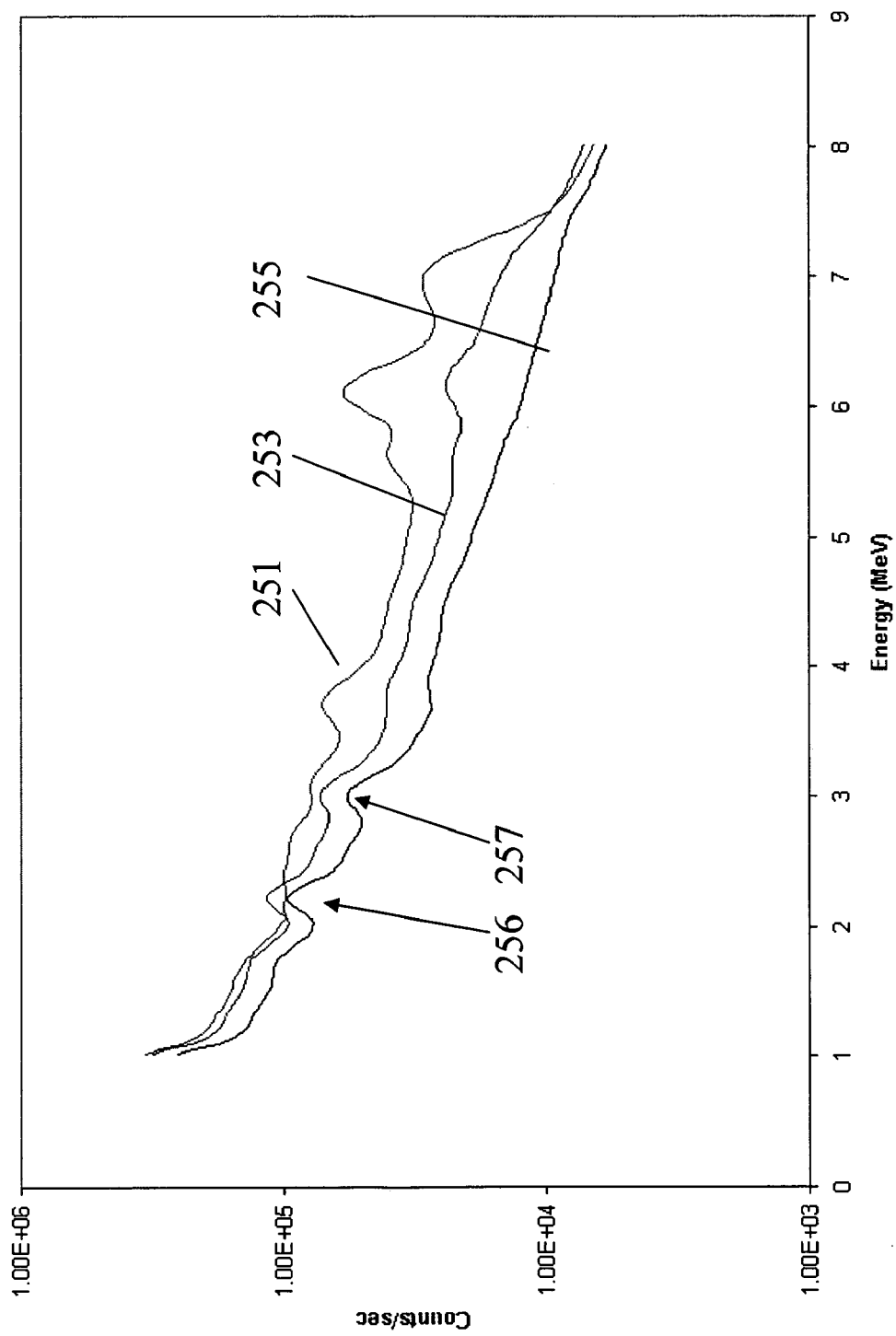
FIG. 6 shows standard spectral measurements relating to Al.

As noted above, one objective of the present invention is the determination of the weight fraction of Al in an earth formation. In order to do so, measurements are made with the logging tool that enable the inelastic spectrum of Al to be recorded. FIG. 6 shows measurements made with the logging tool in a water tank 251. Also shown in FIG. 6 is the spectrum measured with the logging tool in a block of Al in the water tank 253 and the determined spectrum 255 characteristic of the inelastic scattering spectrum of Al. Two primary energy peaks 256, 257 and other minor peaks are noted in the spectrum. The determined spectrum 255 serves as the basis for the estimation of the weight fraction of Al in earth formation in the method of the present invention.

It is worth pointing out that the Herron '057 patent assumes that the Al and Iron (Fe) spectra are correlated, and uses this as a basis for determining the weight fraction of Al. This implicitly assumes that the spectra for Al cannot be readily determined, and other empirical factors, specifically a correlation between the two spectra, are necessary to be able to estimate the Al weight fraction. It has also been the experience of the inventors that the capture spectrum of Al is, in fact, difficult to determine. It is believed that the reason the spectrum for Al has been measured by the present inventors may be because the logging tool used in the invention has a 3×6 inch BGO detector and is used under open-hole conditions. Prior art devices have generally used inelastic spectrum measurements using a pulsed neutron source in cased-hole where the effect of casing can mask the signal from Al.

Figure 7:
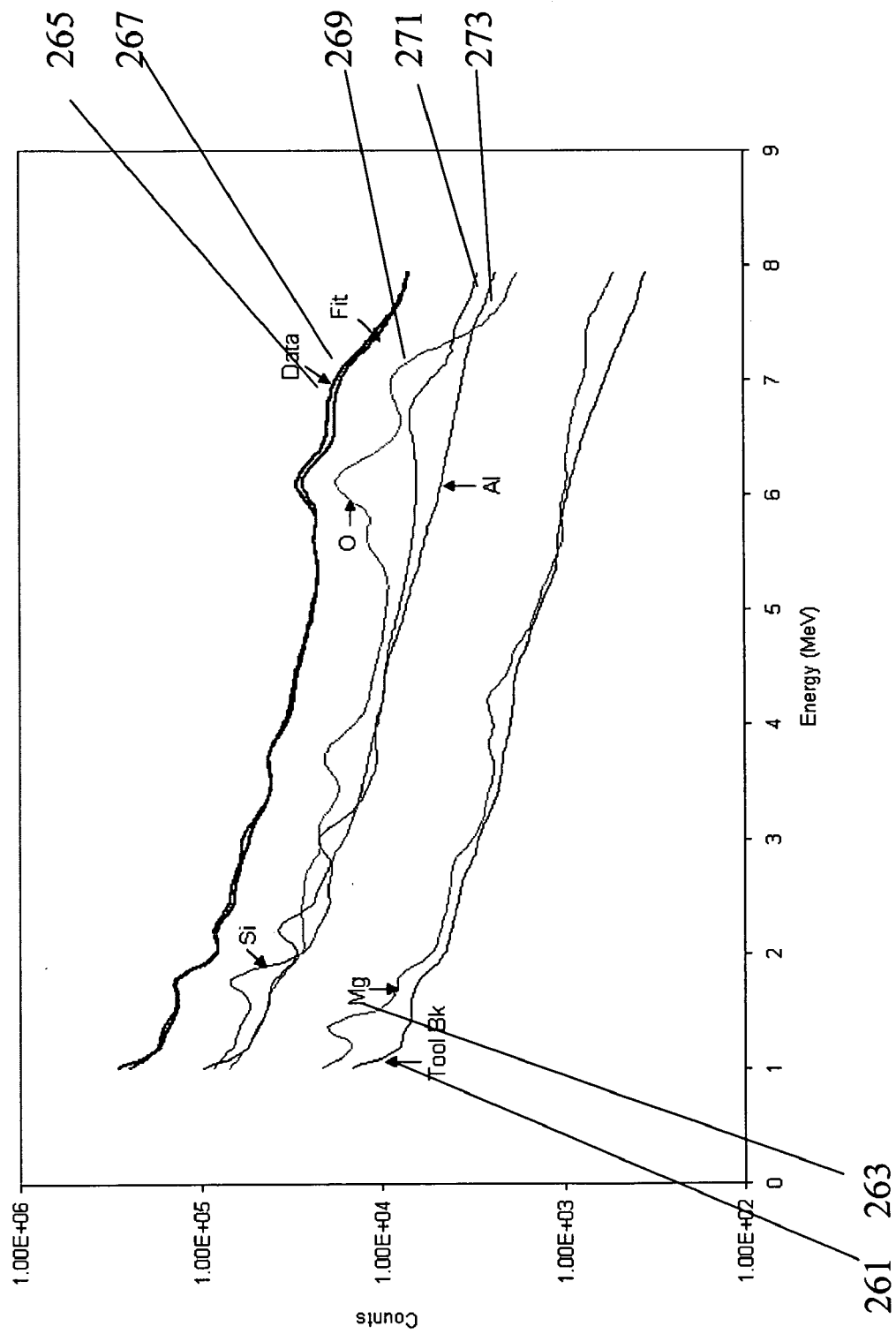
FIG. 7 shows the elemental spectra used in analysis of the intermediate igneous block.

Turning now to FIG. 7, results of using the Al spectrum 255 in the intermediate igneous block are shown. Plotted in FIG. 7 are the tool background signal 261, and the known inelastic spectrum for Magnesium (Mg) 263, Silicon (Si) 271, Oxygen (O) 269, and Al 273 which are the spectral components used in analysis of the spectrum. The measured spectrum for the intermediate igneous block 265 is almost indistinguishable from the best fit obtained by representing the total spectrum as a weighted combination of the known, individual spectra. The weights for the individual spectra are, of course, indicative of the weight fractions of the individual elements in the formation. As would be known to those versed in the art, it is common to choose the elements for the elemental analysis from a priori knowledge of the lithology of the formation.

Figure 8:
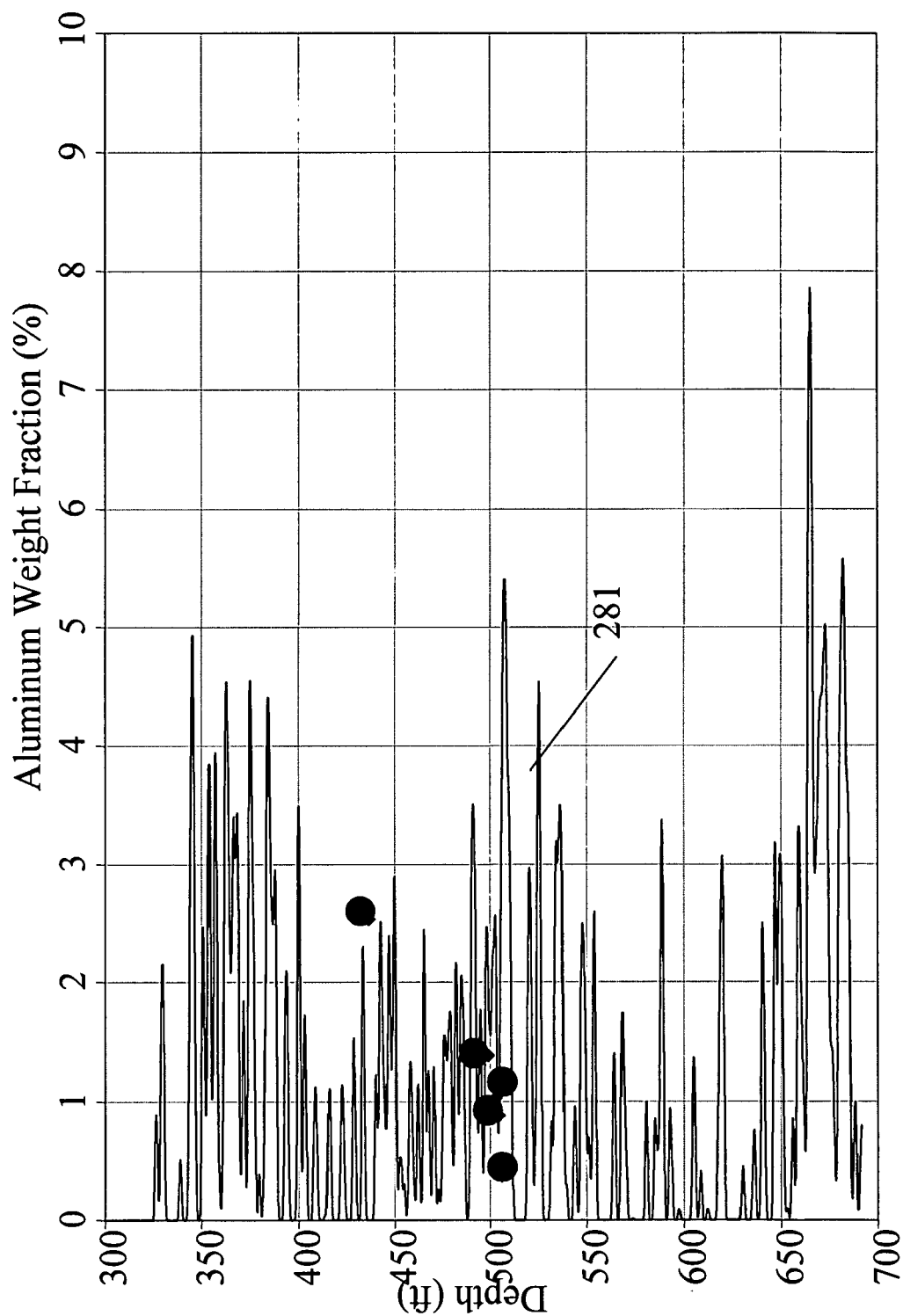
FIG. 8 shows a comparison between weight fractions of Al measured using the method of the present invention with core analysis.

FIG. 8 shows the result of applying the method of the present invention to the determination of Al in an earth formation over a depth interval of approximately 400 ft. The curve 281 is the determined weight fraction of Al. Also plotted in the figure are isolated points representing Al weight fraction determinations made on core samples recovered from the borehole. Agreement between the core measurements and the log measurements is good.

A library of elemental basis functions can be used to enable a decomposition of at least one of capture and inelastic spectra into their respective constituent spectra. A partial list of elements includes H, C, O, S, Al, Ca, Cl, Fe, Mg, Si. Currently, constituent spectra representing up to 20 elements are usable in the present invention. When the fraction of a particular element obtained from both the capture and inelastic spectrum are reasonably close, then their average value may be used for the elemental analysis. Large differences between estimates for a particular element obtained by capture and inelastic spectral decomposition should serve as a cautionary flag. As part of the spectral decomposition using basis functions, it is standard practice to also estimate uncertainties along with the regression coefficients. These uncertainties can be used to provide an estimate of the amount of an element from the individual estimates obtained from inelastic and capture spectra. The number of elements can be increased and is not meant as a limitation of the present invention. Elemental basis functions could further be produced using various methods. For example, use of a computer can enable generation of an elemental basis function of a previously unlisted element.

The elements that can be readily measured from the capture gamma ray energy spectrum comprise Ca, Cl, H, Fe, Mg, Si, and S. The elements that can be readily measured from the inelastic gamma ray energy spectrum comprise C, Ca, Fe, Mg, O, Si, Al and S. The list is not intended to be complete and other elements could also be identified. In some cases, the same element can be determined from both the capture and inelastic spectra. Those elements found in both the capture and inelastic spectra further aid a log analyst in the final scientific interpretation of the data.

Once a gamma ray spectrum is extracted for an individual element, it can be used as an elemental standard. These standards are determinable, for example, using a combination of empirical data from known formations in the Nuclear Instrument Characterization Center, and using computer simulations employing detailed physical modeling techniques. The combination of these standards that results in the best fit to the measured spectra determines the elemental yields.

The elemental determination can be used for mineral identification using the method described in the parent application Ser. No. 10/916,921 of Madigan et al. Mineral identification can be derived from elemental yields using the method of Madigan. Some typical mineral compositions are listed in Table 1.

TABLE 1

| Category | Formation Type | Mineral Composition |
|---|---|---|
| General | Sandstone | $SiO_2$ |
|  | Shale | — |
| Clay | Kaolinite | $Al_2O_3$—$2SiO_2$—$2H_2O$ |
|  | Smectite | $Si_4O_{10}(OH)_2$—$nH_2O$ |
| Carbonate | Limestone | $CaCO_3$ |
|  | Dolomite | $CaMg(CO_3)_2$ |
|  | Siderite | $FeCO_3$ |
| Sulfate | Anhydrite | $CaSO_4$ |
| Oxide | Magnetite | $Fe_3O_4$ |
|  | Quartz | $SiO_2$ |
| Mica | Biotite | $K(Mg,Fe)_3(Al,Fe)Si_3O_{10}(OH,F)_2$ |

Various pattern recognition algorithms can be used to decipher the elemental concentrations measured during a logging run. Alternatively, signature recognition methods can be used to decipher elemental concentrations. An example of such patterns can be observed in Table 2, in which similar measurements were made during a feasibility study. The formations measured for the example of Table 2 possess zero porosity and a 7⅞-inch borehole. An operator versed in the arts can use information from Table 3 for determination of mineral type. As an example, sandstone can be distinguished from limestone. Note, for example, that the 0 pu sandstone formation shows large fractions of silicon whereas the corresponding limestone and dolomite formations do not. As a further example, the magnesium signature in the dolomite formation enables an operator to distinguish dolomite from limestone.

TABLE 2

| Spectrum | Formation | C | Ca | Fe | H | Mg | O | Si |
|---|---|---|---|---|---|---|---|---|
| Capture | Dolomite |  | 0.62 | 0.02 | 0.24 | 0.10 |  | 0.03 |
| Capture | Limestone |  | 0.75 | 0.00 | 0.23 | 0.00 |  | 0.00 |
| Capture | Sandstone |  | 0.01 | 0.01 | 0.35 | 0.02 |  | 0.63 |
| Inelastic | Dolomite | 0.07 | 0.18 |  |  | 0.06 | 0.43 | 0.04 |
| Inelastic | Limestone | 0.08 | 0.40 |  |  | 0.00 | 0.37 | 0.00 |
| Inelastic | Sandstone | 0.00 | 0.01 |  |  | 0.01 | 0.34 | 0.51 |

One embodiment of the invention is based on recognition that going from the elemental analysis to Table 1 (the mineralogical makeup of the rock) can be analyzed as a problem in Linear Programming (LP). The LP problem can be formulated as follows: Maximize an objective function z:

$$z = \sum_{j=1}^{m} X_j \quad (1)$$

subject to a set of n constraints (linear inequalities) of the general form:

$$b_i \geq \sum_{j=1}^{m} a_{ij} X_j, \quad (i = 1, n) \quad (2)$$

and to a set of m basic constraints (linear inequalities) of the form:

$$X_j \geq 0 \; (j=1,m) \quad (3).$$

In the context of the present invention, $X_j$ is the abundance of mineral j in the rock, $b_i$ is the amount element i in the rock, and $a_{ij}$ is the weight ratio of element i in mineral j. The use of the basic (non-negativity) constraints given by eqn. (3) clearly distinguishes this method from the regression analysis used by Herron in which physically unrealistic results are possible in the absence of such constraints.

Eqn. (1) dictates that the total mineral abundance be maximized. It is to be noted that LP can also be used to minimize an objective function. Ideally, if all the elements have been analyzed with absolute accuracy, and if the presence and exact composition of all the minerals in the rock were known, the z should be equal to 100% by weight. In practice, z may be less than 100%. Eqn. (2) is made up of greater-than-or-equal-to ($\geq$) relationships. This accounts for the possibility that a fraction of the elements may be tied up either in minerals not considered, or in amorphous or organic phases.

In the real world, the constraints can be a mixture of inequality constraints ($\geq$, $\leq$) as well as equality constraints. Eqn. (3) simply requires that the amount of a mineral cannot be negative. Solution of eqns. (1)-(3) is a standard problem in Linear Programming and can be found in any textbook on the subject. The most commonly used method for solving LP problems is the Simplex method.

A related problem using a related method is solved in Caritat et al. "LPNORM: A Linear Programming Normative Analysis Code". The problem solved in Caritat is to determine the mineralogy of a rock, but instead of starting with an elemental analysis, the starting point includes measurements of relative abundance of oxides. In the example shown in Caritat, the basic measurements are of the relative oxide abundance, specifically abundance of $SiO_2$, $Al_2O_3$, $Fe_2O_3$, MgO and $K_2O_3$. Given this oxide constituent analysis, the relative fractions of quartz, kaolinite, chlorite and illite were determined. The composition of quartz and kaolinite is fixed (quartz being $SiO_2$ while kaolinite is $Al_2Si_2O_5(OH)_4$. Chlorite and illite can have variable elemental composition, but Caritat assumes illite and chlorite to be $K_{0.96}Fe_{0.31}Mg_{0.28}Al_{1.97}Si_{3.46}O_{10}(OH)_2$ and $Fe_3Mg_2Al_2Si_3O_{10}(OH)_8$ respectively. For this particular example, Caritat shows that a modified LP problem referred to as LPNORM solution works satisfactorily.

The modification made to the standard LP problem in the implementation of LPNROM is the replacement of inequality constraints given by eqns. (2) and (3) by equalities by using auxiliary variables. Specifically, in LPNORM, the objective function is of the form:

$$z = \sum_{j=1}^{m} X_j - \sum_{i=1}^{n} \lambda_i \quad (5)$$

subject to a set of n constraints of the form $$b_i \geq \sum_{j=1}^{m} a_{ij} X_j, +\lambda_i \quad (i = 1, n) \quad (6)$$

and to a set of m+n basic constraints $$X_j \geq 0 \; (j=1,m); \lambda_i \geq 0, (i=1,n). \quad (7)$$

where the $\lambda_i$ are slack variables. The slack variable represents the amount of any element that cannot be accounted for. The sum of the slack variables is an indication of how well the mineral composition of the rock fits the elemental composition.

It should be emphasized that conceptually, for the purposes of the LP method, there is little difference between going from an oxide analysis to a mineralogy, as was done by Caritat, and in going from an elemental analysis to a mineralogy as is done in the present invention. In the context of formation evaluation, most of the earth formations encountered in the earth fall into one of three categories: sandstones, carbonates, and clay (or shale minerals). Reservoir rocks are typically either sandstones or carbonates, the latter being further subdivided into limestone and dolomite. In the process of dolomitization, magnesium ions replace calcium ions in calcite, forming the mineral dolomite. The size of the magnesium atom is less than that of the calcium atom, so the replacement of calcite by dolomite in a rock increases the pore space in the rock by 13%. Consequently, dolomites are an important reservoir rock. The dolomitization can be partial or complete, so that knowledge of the relative fractions of dolomite and calcite in a particular rock is useful in evaluating its reservoir potential. This is done in the method of the present invention.

In sandstone reservoirs, it is common to find clay minerals that can greatly reduce the permeability of the rock with little effect on porosity. The amount of clay minerals can be determined from a natural gamma ray log (that measures the radioactivity of potassium in the clay minerals). The method of the present invention provides additional information about the presence of clay minerals in sand formations without having to run permeability tests that are time consuming.

In applying the method of the present invention, use is made of as much a priori information as possible in defining the possible list of minerals that are to be identified. This information can come from geologic and petrophysical information. The geologic information can come from either on a basin wide scale, or on a prospect scale (from other wells). Information can also come from the same well using sequence stratigraphy principles. This can help exclude certain minerals. For example, in carbonate rocks, due to the geologic setting in which they are formed, in most instances $SiO_2$ can be ruled out as a possible mineral and the most likely minerals are limestone, dolomite and, to a lesser extent, halite, anhydrite and gypsum. Possible presence of clay minerals can be obtained from petrophysical information such as background gamma ray logs. In sedimentary formations, on the other hand, $SiO_2$ and clay minerals are likely to be present, and minerals like limestone, dolomite, halite, anhydrite and gypsum are unlikely to be present. Deletion of extraneous minerals from the candidate minerals greatly speeds up the computation.

The invention has further been described by reference to logging tools that are intended to be conveyed on a wireline. However, the method of the present invention may also be used with measurement-while-drilling (MWD) tools, or logging while drilling (LWD) tools, either of which may be conveyed on a drillstring or on coiled tubing. Further, the invention may be adapted to be conveyed on a slickline, as will be evident to one skilled in the art.

The processing of the data may be done with the use of a computer program implemented on a suitable machine readable medium that enables the processor to perform the control and processing. The term processor as used in this application is used in its traditionally-broad sense and is intended to include such devices as single-core computers, multiple-core computers, distributed computing systems, field programmable gate arrays (FPGAs) and the like. The machine readable medium referenced in this disclosure is any medium that may be read by a machine and may include magnetic media, RAM, ROM, EPROM, EAROM, flash memory and optical disks. The processing may be done downhole or at the surface. In an alternative embodiment, part of the processing may be done downhole with the remainder conducted at the surface.

While the foregoing disclosure is directed to the specific embodiments of the invention, various modifications will be apparent to those skilled in the art. It is intended that all such variations within the scope and spirit of the appended claims be embraced by the foregoing disclosure.

What is claimed is:

1. A method of analyzing an earth formation, the method comprising:
   a) conveying a tool into the earth formation;
   b) irradiating the formation with the tool;
   c) detecting gamma rays resulting from interaction of the irradiation of the formation; and
   d) using an inelastic spectrum of Aluminum (Al) for estimating from a spectrum of the gamma rays an elemental concentration of Al in the formation.

2. The method of claim 1 wherein irradiating the formation further comprises using a pulsed neutron source.

3. The method of claim 1 wherein the detected gamma rays comprises at least one of (i) inelastic gamma rays, and (ii) capture gamma rays.

4. The method of claim 1 wherein the spectrum of the gamma rays further comprises an inelastic spectrum.

5. The method of claim 1 further comprising estimating the inelastic spectrum for Al using measurements made in a water tank.

6. The method of claim 1 further comprising:
   (i) defining a set of possible mineral constituents for the earth formation, and
   (ii) solving a constrained optimization problem to determine a relative fraction of each of the possible mineral constituents.

7. The method of claim 6 wherein the constrained optimization problem comprises a Linear Programming (LP) problem.

8. The method of claim 6 wherein the possible mineral constituents are selected from the group consisting of (i) albite, (ii) anorthite, (iii) orthoclase, (iv) microcline, (v) kaolinite, (vi) montmorillonite, (vii) chlorite, (viii) ilite, (ix) muscovite, (x) biotite, and (xii) glauconite.

9. The method of claim 6 further comprising using the determined relative fraction of each of the possible mineral constituents as an indication of at least one of (A) diagenesis, and (B) source rock maturation.

10. An apparatus for evaluating an earth formation, the apparatus comprising:
    a) a tool configured to be conveyed in a borehole in the earth formation, the tool including:
       (A) a radiation source configured to irradiate the earth formation, and
       (B) at least one detector configured to detect gamma rays resulting from interaction of the irradiation with the earth formation;
    and b) a processor configured to:
       (C) determine a spectrum of the detected gamma rays, and
       (D) use an inelastic spectrum of aluminum (Al) to estimate from the determined spectrum an elemental concentration of Al in the formation.

11. The apparatus of claim 10 wherein the radiation source comprises a pulsed neutron source.

12. The apparatus of claim 10 wherein the detected gamma rays comprises at least one of (i) inelastic gamma rays, and (ii) capture gamma rays.

13. The apparatus of claim 10 wherein the determined spectrum comprises an inelastic spectrum.

14. The apparatus of claim 10 further comprising a device configured to measure the inelastic spectrum for Al.

15. The apparatus of claim 10 wherein the processor is further configured to:
   (i) define a set of possible mineral constituents for the earth formation, and
   (ii) solve a constrained optimization problem to determine a relative fraction of each of the possible mineral constituents.

16. The apparatus of claim 15 wherein the constrained optimization problem comprises a Linear Programming (LP) problem.

17. The apparatus of claim 15 wherein the processor is further configured to select the possible mineral constituents from the group consisting of (i) albite, (ii) anorthite, (iii) orthoclase, (iv) microcline, (v) kaolinite, (vi) montmorillonite, (vii) chlorite, (viii) ilite, (ix) muscovite, (x) biotite, and (xii) glauconite.

18. The apparatus of claim 15 wherein the processor is further configured to use the determined relative fraction of each of the possible mineral constituents as an indication of at least one of (A) diagenesis, and (B) source rock maturation.

19. The apparatus of claim 10 further comprising a conveyance device configured to convey the tool into the borehole, the conveyance device selected from the group consisting of (i) a wireline, (ii) a drilling tubular, and (iii) a slickline.

20. The apparatus of claim 10 wherein the borehole comprises an open-hole.

21. A computer readable medium used with an apparatus for evaluating an earth formation, the apparatus comprising:
   a) a tool configured to be conveyed in a borehole in the earth formation, the tool including:
      (A) a radiation source configured to irradiate the earth formation, and
      (B) at least one detector configured to detect gamma rays resulting from interaction of the irradiation with the earth formation;
   the medium comprising instructions which enable a processor to
   (b) determine a spectrum of the detected gamma rays; and
   (c) use an inelastic spectrum of aluminum (Al) to estimate from the determined spectrum an elemental concentration of Al in the earth formation.

22. The medium of claim 21 further comprising at least one of (i) a ROM, (ii) a CD-ROM, (iii) an EPROM, (iv) an EAROM, (v) a flash memory, and (vi) an optical disk.

* * * * *